United States Patent
Chen et al.

(10) Patent No.: US 10,648,943 B2
(45) Date of Patent: May 12, 2020

(54) REFRIGERANT ANALYZER AND A METHOD OF USING THE SAME

(71) Applicant: Carrier Corporation, Jupiter, FL (US)

(72) Inventors: Lei Chen, South Windsor, CT (US); Zhiwei Yang, South Windsor, CT (US); Warren Clough, Cicero, NY (US); Ivan Rydkin, Rochester, NY (US)

(73) Assignee: CARRIER CORPORATION, Palm Beach Gardens, FL (US)

( * ) Notice: Subject to any disclaimer, the term of this patent is extended or adjusted under 35 U.S.C. 154(b) by 351 days.

(21) Appl. No.: 15/548,378

(22) PCT Filed: Feb. 2, 2016

(86) PCT No.: PCT/US2016/016146
§ 371 (c)(1),
(2) Date: Aug. 2, 2017

(87) PCT Pub. No.: WO2016/126692
PCT Pub. Date: Aug. 11, 2016

(65) Prior Publication Data
US 2018/0017519 A1  Jan. 18, 2018

Related U.S. Application Data

(60) Provisional application No. 62/110,887, filed on Feb. 2, 2015.

(51) Int. Cl.
*G01N 27/406* (2006.01)
*F25B 49/00* (2006.01)
(Continued)

(52) U.S. Cl.
CPC ......... *G01N 27/4065* (2013.01); *F25B 49/00* (2013.01); *G01N 27/4074* (2013.01);
(Continued)

(58) Field of Classification Search
CPC ............ G01N 27/4065; G01N 27/407; G01N 27/4074; G01N 27/4076; G01N 27/4141;
(Continued)

(56) References Cited

U.S. PATENT DOCUMENTS

| | | |
|---|---|---|
| 1,710,933 A | 4/1929 | Lobdell et al. |
| 1,864,544 A | 6/1932 | Lamb |

(Continued)

FOREIGN PATENT DOCUMENTS

| | | |
|---|---|---|
| CN | 203479740 U | 3/2014 |
| EP | 2056044 A1 | 5/2009 |

(Continued)

OTHER PUBLICATIONS

European Patent Office, International Search Report, dated May 13, 2016.

(Continued)

*Primary Examiner* — Susan D Leong
(74) *Attorney, Agent, or Firm* — Cantor Colburn LLP

(57) ABSTRACT

A refrigerant analyzer including a pump, a filtering device, a temperature/humidity regulator, an electrochemical sensor, and a control device, wherein the refrigerant analyzer is configured to circulate conditioned air through the sensing chamber for an initialization duration of time to obtain an initial output value, determine whether the initial output value is stabilized below a predetermined initial limit, circulate a refrigerant through the sensing chamber for a sensing duration of time, operate the control device to measure a sensed output value, and operate the control device to determine a measured concentration of at least one contaminant within the refrigerant based on the sensed output value.

24 Claims, 4 Drawing Sheets

(51) Int. Cl.
*G01N 27/407* (2006.01)
*G01N 33/00* (2006.01)
*G01N 27/417* (2006.01)

(52) U.S. Cl.
CPC ....... *G01N 27/417* (2013.01); *G01N 33/0006* (2013.01); *F25B 2400/12* (2013.01)

(58) Field of Classification Search
CPC .......... G01N 33/0006; G01N 33/0004; G01N 33/0049; G01N 33/0052; G01N 33/0063; G01N 33/0065; F25B 49/00; F25B 2400/12; G01M 3/16
See application file for complete search history.

(56) References Cited

U.S. PATENT DOCUMENTS

| | | |
|---|---|---|
| 5,351,037 A | 9/1994 | Martell et al. |
| 5,363,661 A | 11/1994 | Condit et al. |
| 5,425,869 A | 6/1995 | Noding et al. |
| 5,624,546 A | 4/1997 | Milco |
| 8,650,953 B2 | 2/2014 | Cherian et al. |
| 8,741,120 B2 | 6/2014 | Chapples et al. |
| 2002/0092341 A1 | 7/2002 | Cardinale et al. |
| 2003/0143446 A1* | 7/2003 | Faris .................... H01M 4/42 429/404 |
| 2012/0079871 A1 | 4/2012 | Williamson |
| 2014/0356971 A1 | 12/2014 | Kozlow et al. |
| 2015/0027906 A1 | 1/2015 | Chen et al. |
| 2016/0178229 A1* | 6/2016 | Chen .................... G01M 3/228 62/56 |

FOREIGN PATENT DOCUMENTS

| | | |
|---|---|---|
| EP | 2667190 A2 | 11/2013 |
| GB | 2369888 A | 6/2002 |
| JP | H08292169 A | 11/1996 |
| JP | 2006120825 A | 5/2006 |
| WO | 2008109933 A1 | 9/2008 |

OTHER PUBLICATIONS

European Patent Office, Written Opinion of the International Searching Authority, dated May 13, 2016.
Chinese Office Action for application 201680011056.4, dated May 15, 2019, 6 pages.
Japanese Office Action for appiication JP 2017-559282, dated Nov. 5, 2019, translation, 6 pages.

* cited by examiner

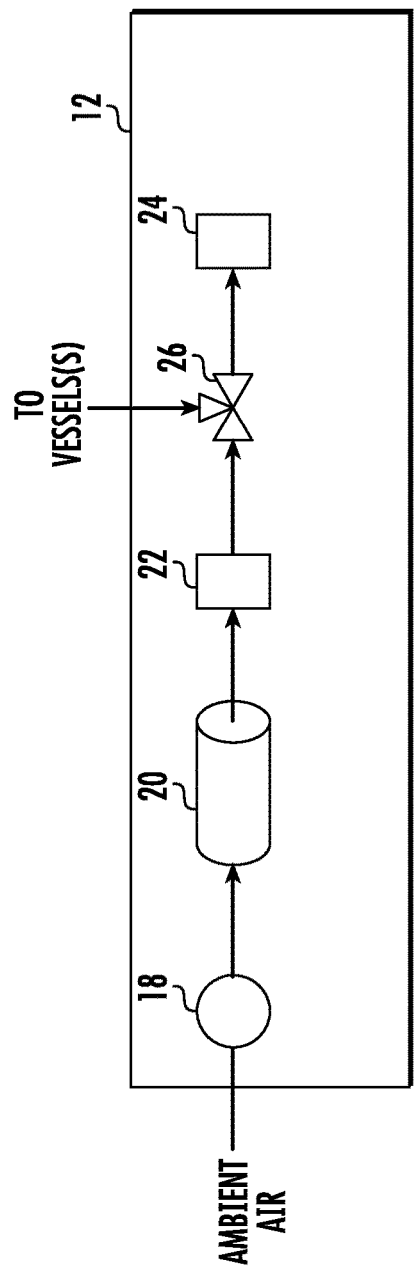
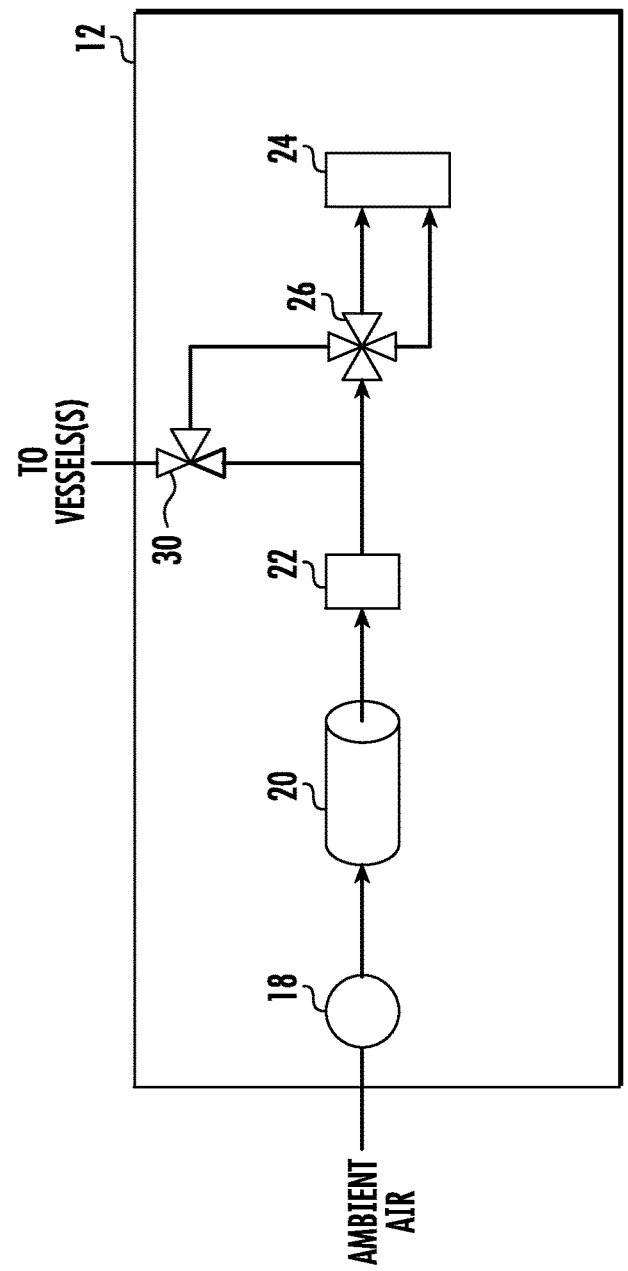

REFRIGERANT ANALYZER AND A METHOD OF USING THE SAME

CROSS REFERENCE TO RELATED APPLICATIONS

The present application is a U.S. national stage of, and claims the priority benefit of, International Patent Application Serial No. PCT/US2016/016146, filed Feb. 2, 2016 and also claims the priority benefit of U.S. Application Ser. No. 62/110,887 filed Feb. 2, 2015, the text and drawings of which are hereby incorporated by reference in their entireties.

TECHNICAL FIELD OF THE DISCLOSED EMBODIMENTS

The presently disclosed embodiments generally relate to devices used for identification and analysis of gaseous impurities in refrigerant gas and more particularly, to a refrigerant analyzer and a method of using the same.

BACKGROUND OF THE DISCLOSED EMBODIMENTS

Counterfeit refrigerants, such as methyl chloride (R40), have been found in refrigeration systems. R40 is toxic, flammable and reactive with aluminum. Reaction product of R40 with aluminum has been identified as trimethyl aluminum, which can burn spontaneously in the presence of air. There is therefore a need for a device to aid in the detection of counterfeit refrigerants, namely R40.

SUMMARY OF THE DISCLOSED EMBODIMENTS

In one aspect, a refrigerant analyzer is provided. The refrigerant analyzer includes a pump operably coupled to a filtering device. The filtering device is operably coupled to a temperature/humidity regulator, and the temperature/humidity regulator is operably coupled to an electrochemical sensor.

The electrochemical sensor includes a membrane electrode assembly (MEA) consisting of a solid polymer electrolyte (SPE) disposed between sensing electrode and counter electrode. Current collectors/gas diffusion media are attached to the electrodes and are connected to circuit, which includes a measurement and/or control device. A housing includes openings for refrigerant to flow therethrough. In one embodiment, the electrochemical sensor further includes a sealed chamber, which also contains a liquid material such as an aqueous salt or acid solution, which can be isolated from contact with the counter electrode by a gas-permeable membrane. The liquid material is configured to regulate a humidity value within the sealed chamber. In one embodiment, the humidity value is less than or equal to approximately 60 percent relative humidity.

In one aspect, a method for detecting impurities within a refrigerant is provided. The method includes the step of circulating conditioned air through the sensing chamber for an initialization period of time to obtain an initial output value. In an embodiment, the initialization period of time is greater than or equal to approximately 5 minutes. The method further includes the step of determining whether the initial output value is stabilized below a pre-determined initial limit. In one embodiment, the pre-determined initial limit is less than or equal to approximately 4 $\mu A/cm^2$.

In one embodiment, the method further includes the step of circulating a first medium through the sensing chamber for a baseline duration of time to obtain a baseline value. In an embodiment, the first medium includes a dry gas. In one embodiment, the baseline duration of time is less than or equal to approximately 3 minutes.

In an alternate embodiment, the method further includes the step of determining whether the baseline value is less than or equal to the initial output value. In an embodiment, if is determined that the baseline value is greater than the initial output value, the method proceeds to determine whether the baseline value is increasing. If the baseline value is increasing, the method ends until the electromechanical sensor is restored to working order.

If the baseline value is less than the initial output value, or the baseline value is greater than the initial output value but is steady, the method proceeds to the step of circulating a refrigerant through the sensing chamber for a sensing duration of time. In an embodiment, the sensing duration of time is less than or equal to approximately 3 minutes.

The method further includes the step of operating the control device to measure a sensed output value. In one embodiment, the sensed output value comprises an electric current density value.

The method further includes the step of operating the control device to determine a measured concentration of at least one contaminant within the refrigerant based on the sensed output value. In one embodiment, the measured concentration comprises the transformed difference between the sensed output value and the initial output value. In another embodiment, the measured concentration comprises the transformed difference between the sensed output value and the baseline value.

In one embodiment, the method includes the step of operating the control device to produce a signal indicative of the presence of at least one contaminant. In an embodiment, the at least one contaminant includes methyl chloride. In one embodiment, the presence of methyl chloride includes a measured concentration greater than or equal to approximately 0.5 percent of the refrigerant tested. In one embodiment, the signal is selected from a group consisting of an audio and a visual signal.

BRIEF DESCRIPTION OF THE DRAWINGS

The embodiments and other features, advantages and disclosures contained herein, and the manner of attaining them, will become apparent and the present disclosure will be better understood by reference to the following description of various exemplary embodiments of the present disclosure taken in conjunction with the accompanying drawings, wherein:

FIG. 2A-2B illustrate schematic diagrams of a refrigerant analyzer according to embodiments of the present disclosure;

DETAILED DESCRIPTION OF THE DISCLOSED EMBODIMENTS

Figure 1:
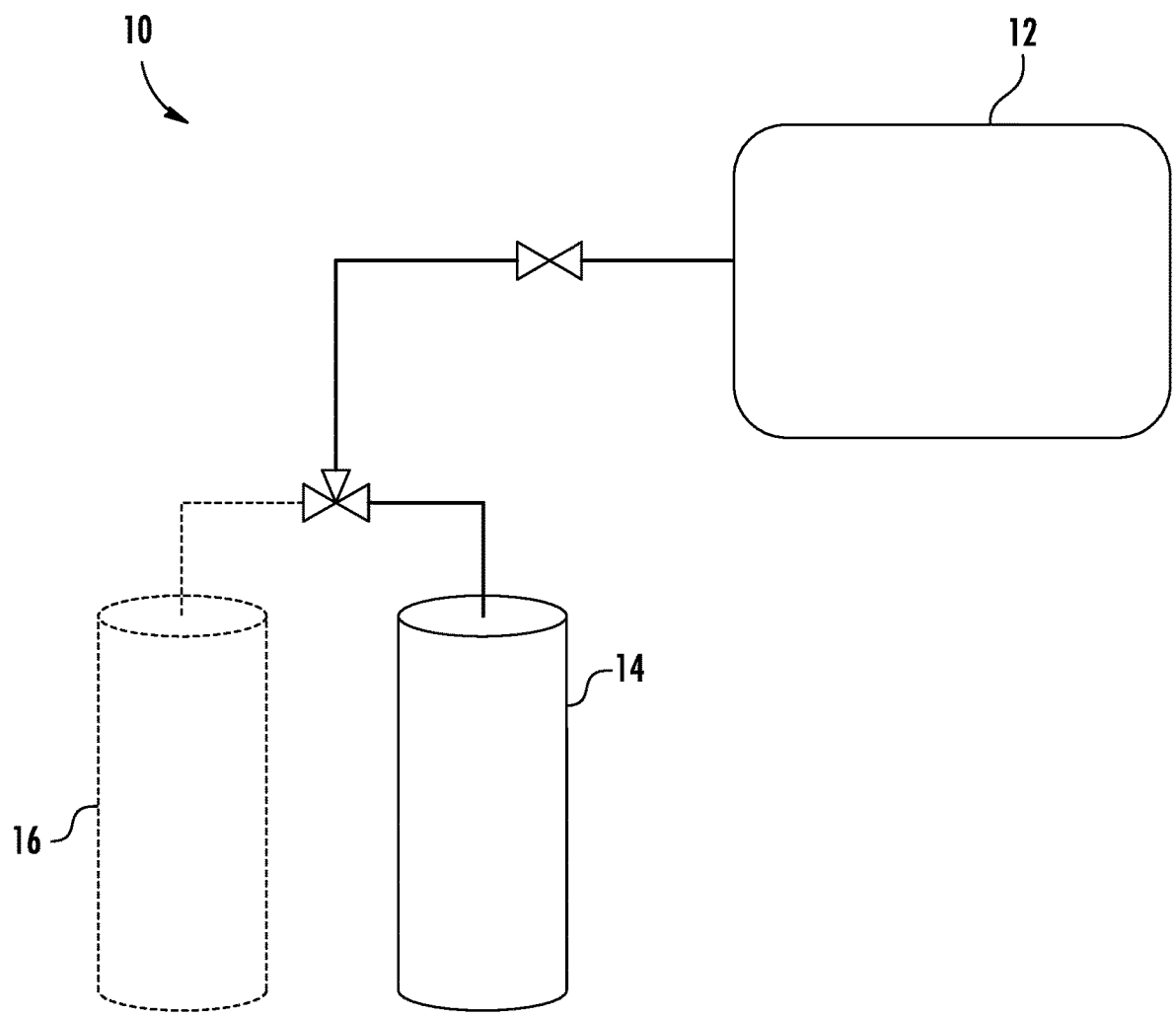
FIG. 1 illustrates a schematic diagram of a system for detecting impurities within a refrigerant according to an embodiment of the present disclosure.

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

FIG. 1 illustrates an embodiment of a system for detecting impurities within a refrigerant, namely methyl chloride, the system generally indicated at 10. The system 10 includes a refrigerant analyzer 12 operably coupled to a refrigerant vessel 14 to analyze the refrigerant stored therein. In one embodiment, the refrigerant analyzer 12 is further coupled to a first medium vessel 16. In one embodiment, the first medium includes a dry gas, for example, air, nitrogen, or 1,1,1,2-Tetrafluoroethane (i.e. R-134a) to name a few non-limiting examples.

FIGS. 2A and 2B illustrate embodiments of the refrigerant analyzer 12. The refrigerant analyzer 12 includes a pump 18, for example an air pump, operably coupled to a filtering device 20. The filtering device 20 is operably coupled to a temperature/humidity regulator 22, and the temperature/humidity regulator 22 is operably coupled to an electrochemical sensor 24 via a valve 26. In one embodiment, as shown in FIG. 2B, the temperature/humidity regulator 22 is further coupled to a valve 30. The pump 18 is configured to circulate ambient air through the filtering device 20 and into the temperature/humidity regulator 22. The filtering device 20 is configured to remove particles and gaseous species from the air received from pump 18. The temperature/humidity regulator 22 is configured to regulate a humidity value of the filtered air supplied to the electrochemical sensor 24 though valve 26.

Figure 3A:
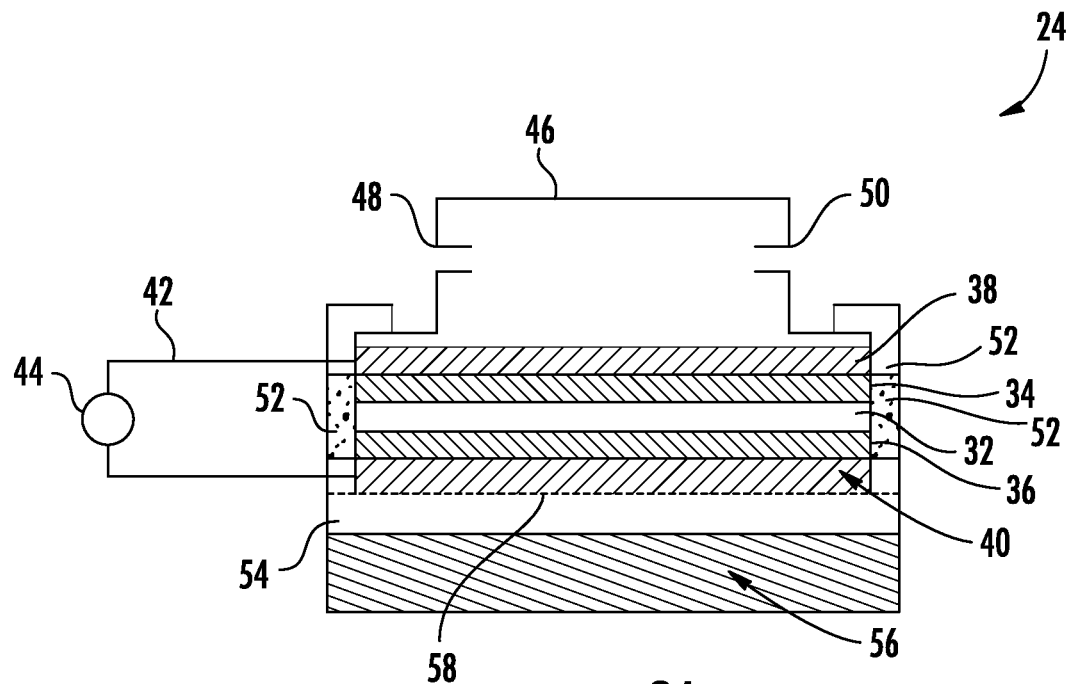
FIG. 3A-3B illustrate schematic diagrams of an electrochemical sensor according to embodiments of the present disclosure.
Figure 3B:
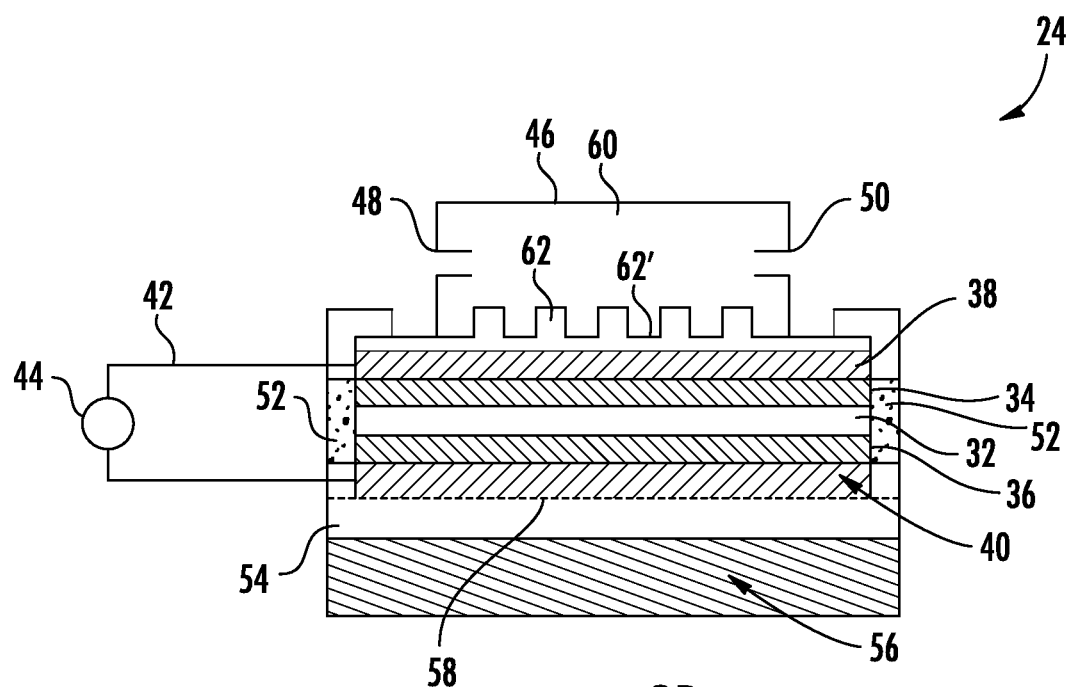

FIGS. 3A-3B illustrate embodiments of the electrochemical sensor 24 contained within the refrigerant analyzer 12. In the embodiments shown, the electrochemical sensor 24 includes a membrane electrode assembly (MEA) consisting of a solid polymer electrolyte (SPE) (i.e., ion conducting polymer or ion conducting polymer infiltrated porous matrix) 32 disposed between sensing electrode 34 and counter electrode 36. Current collectors/gas diffusion media 38 and 40 are attached to the electrodes and are connected to circuit 42, which includes a measurement and/or control device 44. In some embodiments, an optional reference electrode (not shown) may be in contact with the SPE 32 and electrically connected to measurement and/or control device 44 in order to monitor the potential of the sensing electrode 34 and/or counter electrode 36. Housing 46 includes openings 48 and 50 for refrigerant to flow therethrough. The edges of the MEA are sealed against seal 52 formed of a seal material such as rubber, to name just one non-limiting example. The seal 52 ensures that the test gas and reference gas are maintained on opposing sides of the MEA, although other techniques known in the art (e.g., disposing the electrochemical sensor 24 in a frame (not shown) that is sealed to the edges of the housing) can be used. The current collectors 38, 40 can be formed from a porous conductive mesh or felt, and are depicted with thickness so that they can also function as gas diffusion media enabling the refrigerant tested and reference gas (i.e. air) to reach the surface of the electrodes 34, 36. The current collector/gas diffusion mediums 38 and 40 associated with the sensing electrode 34 and counter electrode 36, respectively, can be formed from an oxidation-resistant material such as graphitized carbon, titanium, or stainless steel, to name just a few non-limiting examples. Measurement and/or control device 44 can be a voltmeter or ampere meter, but in some embodiments may comprise a potentiostatic circuit, microprocessor, electronic control unit (ECU), or similar electronic device with integrated voltage and or amperage measurement functions and which can also apply a voltage bias between the sensing electrode 34 and counter electrode 36 during operation of the electrochemical sensor 24. In one embodiment, the electrochemical sensor 24 further includes a sealed chamber 54, which also contains a liquid material such as an aqueous salt or acid solution 56, which can be isolated from contact with the counter electrode 36 by a gas-permeable membrane 58. The liquid material is configured to regulate a humidity value within the sealed chamber 56. In one embodiment, the humidity value is less than or equal to approximately 60 percent relative humidity. As shown in FIG. 3B, the electrochemical sensor 24 may also include an endplate 60 having a flow channel 62 and ribs 62' that provide a flow field on the sensing electrode 34. The ribs 62' of the flow channel 62 are pressed against the assembly to maintain electrical contact and seal around the edges of the assembly. While the illustrated electrochemical sensor 24 does not depict the details of a channel with openings associated with the counter electrode 36 to allow air to contact the counter electrode 36, it will be appreciated that the electrochemical sensor 24 may be configured in such a manner.

Figure 4:
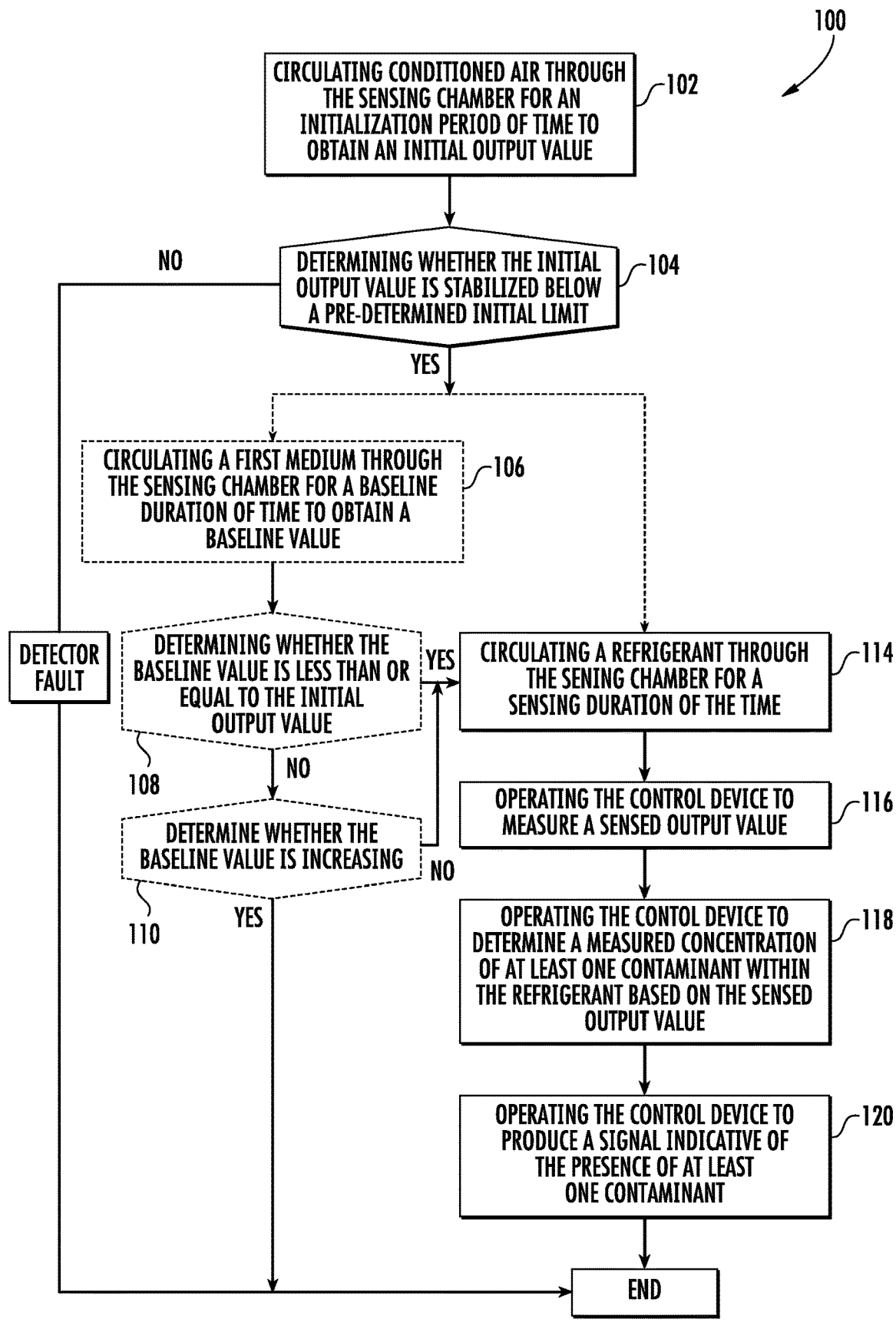
FIG. 4 illustrates a schematic flow diagram of a method for detecting impurities within a refrigerant according to an embodiment of the present disclosure.

FIG. 4 illustrates a schematic flow diagram of a method, generally indicated at 100, for detecting impurities within a refrigerant, namely methyl chloride by utilizing the system 10. The method 100 includes the step 102 of circulating conditioned air through the sensing chamber for an initialization period of time to obtain an initial output value. In one embodiment, the initialization period of time is greater than or equal to approximately 5 minutes. It will be appreciated that in other embodiments, the initialization period of time may be less than approximately 5 minutes. It will be further appreciated that the initialization period of time may vary depending on the ambient temperature and humidity conditions. For example, with reference to FIGS. 2A and 3A, ambient air is directed from the pump 18 through the filtering device 20 and into the temperature/humidity regulator 22. The regulated air flows through valve 26 into and through openings 48, 50 where the regulated air makes contact with the current collector/gas diffusion medium 38 associated with the sensing electrode 34.

The method 100 further includes step 104 of determining whether the initial output value is stabilized below a pre-determined initial limit. In one embodiment, the pre-determined initial limit is less than or equal to approximately 4 $\mu A/cm^2$. For example, with continued reference to FIGS. 2A and 3A, the control device 44 detects the electrical current between the sensing electrode and the counter electrode 36 when the regulated air flows over the sensing electrode 34. If the initial output value cannot remain within the pre-determined range, it is indicative that there may be a fault with the electrochemical sensor 24 and/or the air may contain active contaminant(s). As a result, the method 100 ends until the electromechanical sensor 24 is restored to working order. It will be appreciated that a signal may be generated designating a fault with the electromechanical sensor 24. A steady and low initial output value is indicative that the electrochemical sensor 24 is properly operating without the interference from ambient air contaminants.

In one embodiment, the method further includes step 106 of circulating a first medium through the sensing chamber for a baseline duration of time to obtain a baseline value. In one embodiment, the first medium includes a dry gas. For example, the dry gas may include dry air, nitrogen, or 1,1,1,2-Tetrafluoroethane (R-134a) to name a few non-limiting examples. In one embodiment, the baseline duration of time is less than or equal to approximately 3 minutes. It will be appreciated that in other embodiments the baseline duration of time may be greater than approximately 3 minutes. In one embodiment, the baseline value comprises an electric current density value. For example, with continued reference to FIGS. 2A and 3A, R-134a from first medium vessel 16 may be circulated through valve 26 and through openings 48, 50 where the R-134a makes contact with the current collector/gas diffusion medium 38 associated with the sensing electrode 34 so that the baseline value may be obtained.

In one embodiment, the method 100 further includes the step 108 of determining whether the baseline value is less than or equal to the initial output value from step 102. For example, depending on the first medium that has been chosen, the control device 44 measures the current density from the electrochemical reaction of the first medium flowing over the sensing electrode 34 and the regulated counter electrode 36 to determine whether the chosen first medium is within the known current density specifications for the type of medium.

In one embodiment, if is determined that the baseline value is greater than the initial output value, the method proceeds to step 110 to determine whether the baseline value is increasing. If the baseline value is increasing, the method 100 ends until the electromechanical sensor 24 is restored to working order. It will be appreciated that a signal may be generated designating a fault with the electromechanical sensor 24. If the baseline value is less than the initial output value or the baseline value is greater than the initial output value but is steady, the method proceeds to step 114.

The method 100 further comprises the step 114 of circulating a refrigerant through the sensing chamber for a sensing duration of time. In one embodiment, the sensing duration of time is less than or equal to approximately 3 minutes. It will be appreciated that in other embodiments the sensing duration of time may be greater than approximately 3 minutes. For example, with continued reference to FIGS. 2A and 3A, after it is determined that the baseline value is within the baseline limit, valve 26 operates to allow refrigerant from refrigerant vessel 14 to flow through openings 48, 50.

The method 100 further includes the step 116 of operating the control device 44 to measure a sensed output value. In one embodiment, the sensed output value comprises an electric current density value. For example, with continued reference to FIGS. 2A and 3A, as the refrigerant flows through the sensing chamber, the control device 44 measures the voltage or current at the sensing electrode 34 relative to the counter electrode 36

The method 100 further includes the step 118 of operating the control device 44 to determine a measured concentration of at least one contaminant within the refrigerant based on the sensed output value. In one embodiment, the measured concentration comprises the transformed difference between the sensed output value and the initial output value. In another embodiment, the measured concentration comprises the transformed difference between the sensed output value and the baseline value. For example, after the control device 44 measures the sensed output value from step 116, the control device 24 subtracts the sensed output value from the initial output value from step 102, or from the baseline value obtained in step 106 to determine the concentration of contaminant(s) in the refrigerant tested.

In one embodiment, the method includes the step 120 of operating the control device 44 to produce a signal indicative of the presence of at least one contaminant. In one embodiment, the at least one contaminant includes methyl chloride. It will be appreciated that the control device 44 may operate to also produce a signal indicative of no presence of the at least one contaminant. In one embodiment, the presence of methyl chloride includes a measured concentration greater than or equal to approximately 0.5 percent of the refrigerant tested. In one embodiment, the signal is selected from a group consisting of an audio and a visual signal. For example, if the control device 44 calculates a measured concentration of less than approximately 0.5% methyl chloride, the control device 44 may send an audio or visual signal indicating that no methyl chloride is present in the refrigerant. If the control device 44 calculates a measured concentration of greater than approximately 0.5% methyl chloride, the control device may produce either or both of an audio signal, for example a buzzer, or a visual signal, for example lighting a LED or displaying the numerical measured concentration to name a few non-limiting examples.

It will therefore be appreciated that the present embodiments include a refrigerant analyzer 12 including a electrochemical sensor 24 capable of detecting concentration of at least one contaminant, for example methyl chloride to within both a satisfactory detection limit and with no cross-sensitivity to other hydrochlorofluorocarbons and hydrofluorocarbons.

While the invention has been illustrated and described in detail in the drawings and foregoing description, the same is to be considered as illustrative and not restrictive in character, it being understood that only certain embodiments have been shown and described and that all changes and modifications that come within the spirit of the invention are desired to be protected.

What is claimed is:

1. A method of detecting impurities in a refrigerant utilizing a refrigerant analyzer, wherein the refrigerant analyzer includes an electrochemical sensor operably coupled to a control device, the electrochemical sensor including a counter electrode disposed within an atmospheric regulated chamber and a sensing electrode disposed within a sensing chamber, the method comprising the steps:
    circulating conditioned air through the sensing chamber for an initialization duration of time to obtain an initial output value;
    determining whether the initial output value is stabilized below a pre-determined initial limit;
    circulating a refrigerant through the sensing chamber for a sensing duration of time;
    operating the control device to measure a sensed output value; and
    operating the control device to determine a measured concentration of at least one contaminant within the refrigerant based on the sensed output value.

2. The method of claim 1, wherein the pre-determined initial limit is less than or equal to approximately 4 microamperes per square centimeter.

3. The method of claim 1, further comprising, after step (b) and prior to step (c), circulating a first medium through the sensing chamber for a baseline duration of time to obtain a baseline value.

4. The method of claim 3, further comprising:
    determining whether the baseline value is less than or equal to the initial output value;
    and
    determining whether the baseline value is increasing, if the baseline value is greater than the initial output value.

5. The method of claim 1, wherein step (e) further comprises operating the control device to produce a signal indicative of the presence of contaminant(s) within the refrigerant.

6. The method of claim 1, wherein the initialization duration of time is greater than or equal to approximately 5 minutes.

7. The method of claim 5, wherein the contaminant(s) comprises methyl chloride.

8. The method of claim 7, wherein the presence of methyl chloride comprises a measured concentration greater than or equal to approximately 0.5% of the refrigerant tested.

9. The method of claim 5, wherein the signal is selected from a group consisting of an audio and a visual signal.

10. The method of claim 3, wherein the baseline duration of time is less than or equal to approximately 3 minutes.

11. The method of claim 3, wherein the first medium comprises a dry gas.

12. The method of claim 1, wherein the sensing duration of time is less than or equal to approximately 3 minutes.

13. The method of claim 3, wherein the measured concentration comprises the difference between the sensed output value and the baseline value.

14. The method of claim 1, wherein the measured concentration comprises the difference between the sensed output value and the initial output value.

15. A refrigerant analyzer to detect impurities in a refrigerant comprising:
a pump, wherein the pump is configured to circulate conditioned air;
a filtering device operably coupled to the pump;
an electrochemical sensor, wherein the electrochemical sensor is configured to allow a refrigerant to flow therethrough to establish a sensed output value;
a control device operably coupled to the electrochemical sensor, wherein the control device is configured to measure an initial output value of conditioned air, a baseline value of a first medium, measure the sensed output value of the refrigerant, and determine a measured concentration of at least one contaminant within the refrigerant based on the sensed output value; and
a temperature/humidity regulator operably coupled to the electrochemical sensor and the filtering device, wherein the temperature/humidity regulator is configured to regulate a humidity value.

16. The refrigerant analyzer of claim 15, wherein the electrochemical sensor is further configured to allow the first medium to flow therethrough to establish the baseline value.

17. The refrigerant analyzer of claim 15, where the measured concentration comprises the difference between the sensed value and the initial output value.

18. The refrigerant analyzer of claim 16, wherein the measured concentration comprises the difference between the sensed output value and the baseline value.

19. The refrigerant analyzer of claim 16, wherein the control device is further configured to determine whether the baseline value is less than or equal to the initial output value.

20. The refrigerant analyzer of claim 15, wherein the control device is further configured to produce a signal indicative of the presence of the at least one contaminant within refrigerant.

21. The refrigerant analyzer of claim 20, wherein the at least one contaminant comprises methyl chloride.

22. The refrigerant analyzer of claim 21, wherein the presence of methyl chloride comprises a measured concentration greater than or equal to approximately 0.5% of the refrigerant tested.

23. The refrigerant analyzer of claim 15, wherein the humidity value is less than or equal to approximately 60 percent relative humidity.

24. The refrigerant analyzer of claim 15, wherein the first medium comprises a dry gas.

* * * * *